United States Patent
Bischof et al.

(10) Patent No.: US 9,290,432 B2
(45) Date of Patent: Mar. 22, 2016

(54) PROCESS FOR THE PREPARATION OF TRAVOPROST

(71) Applicant: CHINOIN GYÓGYSZER ÉS VEGYÉSZETI TERMÉKEK GYÁRA ZRT., Budapest (HU)

(72) Inventors: Zoltán Bischof, Budapest (HU); Ádám Bódis, Budapest (HU); Mária Kömüves-Mars, Budapest (HU); Gábor Havasi, Budapest (HU)

(73) Assignee: CHINOIN GYÓGYSZER ÉS VEGYÉSZETI TERMÉKEK GYÁRA ZRT., Budapest (HU)

(*) Notice: Subject to any disclaimer, the term of this patent is extended or adjusted under 35 U.S.C. 154(b) by 0 days.

(21) Appl. No.: 14/648,504

(22) PCT Filed: Nov. 26, 2013

(86) PCT No.: PCT/HU2013/000113
§ 371 (c)(1),
(2) Date: May 29, 2015

(87) PCT Pub. No.: WO2014/083367
PCT Pub. Date: Jun. 5, 2014

(65) Prior Publication Data
US 2015/0291503 A1   Oct. 15, 2015

(30) Foreign Application Priority Data
Nov. 30, 2012   (HU) ...................................... 1200695

(51) Int. Cl.
C07C 67/42 (2006.01)
C07C 405/00 (2006.01)

(52) U.S. Cl.
CPC .............. *C07C 67/42* (2013.01); *C07C 405/00* (2013.01); *C07C 2101/08* (2013.01)

(58) Field of Classification Search
CPC .... C07C 67/42; C07C 405/00; C07C 2101/08
See application file for complete search history.

(56) References Cited

U.S. PATENT DOCUMENTS

| 3,959,319 A | 5/1976 | Morozowich |
| 7,166,730 B2 | 1/2007 | Gutman et al. |
| 2005/0209337 A1* | 9/2005 | Gutman ............... C07C 405/00 514/573 |

FOREIGN PATENT DOCUMENTS

| WO | WO 93/00329 A1 | 1/1993 |
| WO | WO 02/40466 A2 | 5/2002 |
| WO | WO 2010/097672 A1 | 9/2010 |

OTHER PUBLICATIONS

Disadee et al., "Polymer-Supported DMI as a Potential Heterogeneous Dehydrating Agent: Application to Esterification and Amidation", Synlett, 2003, No. 1, pp. 115-117.
International Search Report, issued in PCT/HU2013/000113, dated Apr. 9, 2014.
Isobe et al., "2-Chloro-1,3-dimethylimidazolinium Chloride. 1. A Powerful Dehydrating Equivalent to DCC", Journal of Organic Chemistry, 1999, vol. 64, No. 19, pp. 6984-6988.
Search Report issued in Hungarian priority application P1200695, dated May 29, 2013.
Written Opinion of the International Searching Authority, issued in PCT/HU2013/000113, dated Apr. 9, 2014.

* cited by examiner

*Primary Examiner* — Shailendra Kumar
(74) *Attorney, Agent, or Firm* — Birch, Stewart, Kolasch & Birch, LLP

(57) ABSTRACT

The subject of the invention is process the preparation of travoprost of formula (I) characterized by that the free acid of formula (II) is a.) activated with 2-chloro-1,3-dimethyl-imidazolinium chloride (DMC) and the resulting activated carboxylic acid intermediate is reacted with isopropyl alcohol, or b.) reacted with alkyl haloformate and the resulting mixed anhydride is reacted with isopropyl alcohol, or c.) activated with a straight or branched C1-8 dialkyl dicarbonate and reacted with isopropanol in the presence of water-free magnesium salt.

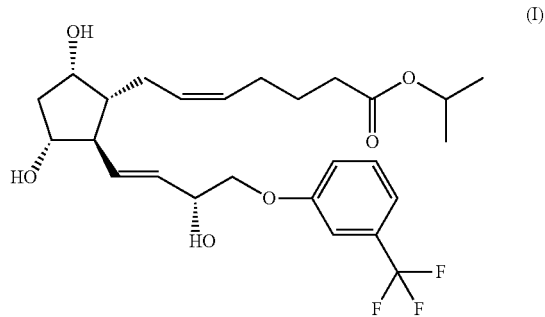

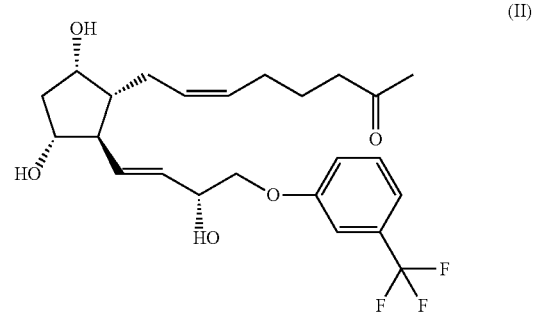

21 Claims, No Drawings

PROCESS FOR THE PREPARATION OF TRAVOPROST

This application is a 371 of PCT/HU2013/000113, filed Nov. 26, 2013.

The subject of our invention is a novel process for the preparation travoprost.

Travoprost of formula (I)

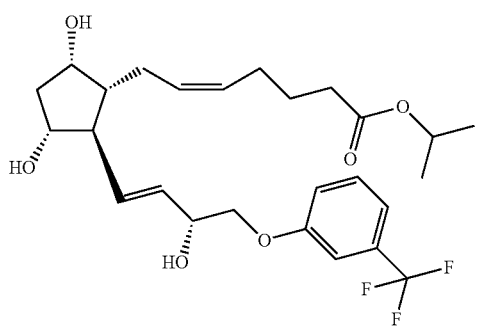

(I)

is a known prostaglandin derivative used in the treatment of glaucoma and high eye pressure (EP0639563A).

In the known processes for the preparation of travoprost (EP 2 143 712A, WO2011046569, U.S. Pat. No. 7,166,730) the ester group is formed by reacting the free acid with an active alkyl derivative, as for instance alkyl halogenide or alkyl sulfate, in the presence of a strong base.

As strong base, among others potassium carbonate, cesium carbonate, 1,8-diazabicyclo[5.4.0]undec-7-ene are applied. Using cesium carbonate the reaction proceeds through the cesium salt. As solvent, the processes generally apply dimethyl formamide.

Disadvantage of the process is that alkyl halogenides or alkyl sulfates are toxic, therefore their use is avoidable because of high safety and environmental risks.

The aim of our invention is to provide new way for the preparation of travoprost avoiding the drawbacks of the known synthetic routes.

In the process according to our invention, travoprost of formula (I) may be prepared in a way that the free acid ("travoprost acid") of formula (II) is

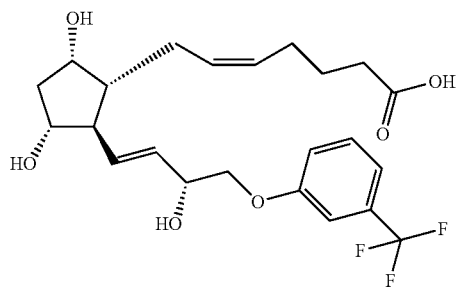

(II)

a.) activated with 2-chloro-1,3-dimethylimidazolinium chloride (DMC) and the resulting activated carboxylic acid intermediate is reacted with isopropyl alcohol, or b.) activated with a straight or branched $C_{1-6}$ alkyl haloformate and the resulting mixed anhydride is reacted with isopropyl alcohol, or c.) activated with a straight or branched $C_{1-8}$ dialkyl dicarbonate and reacted with isopropyl alcohol in the presence of water-free magnesium salt.

According to our invention the alcohol component—isopropyl alcohol—may also be activated to accelerate the reaction. Activation of the alcohol component may be carried out with metal alcoholates, as for metal alcoholate for example potassium tertiary-butoxide may be used.

In methods a.) and b.) according to our invention instead of dimethyl formamide polar aprotic, aromatic, halogenated, ester- or ether-type solvents, preferably the appropriate alcohol may be used as solvent, whereas in method c.) acetonitrile may be used as solvent.

To form the isopropyl ester, instead of the toxic alkyl halogenide reagents known from the literature, the process according to our invention uses the alcohol itself as reagent and the applied activating agent is not toxic, either.

The full synthesis according to method a.) is demonstrated in FIG. 1.

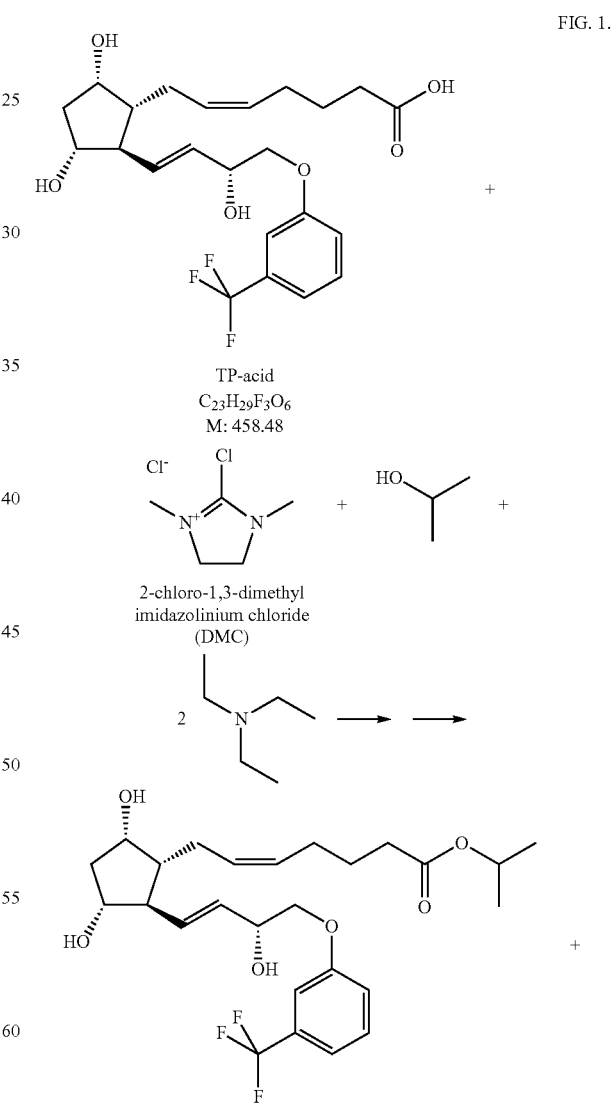

FIG. 1.

-continued

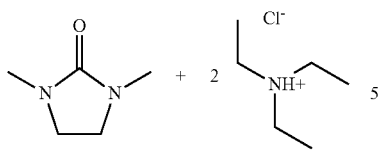

The full synthesis according to method b.) is demonstrated in FIG. 2.

FIG. 2.

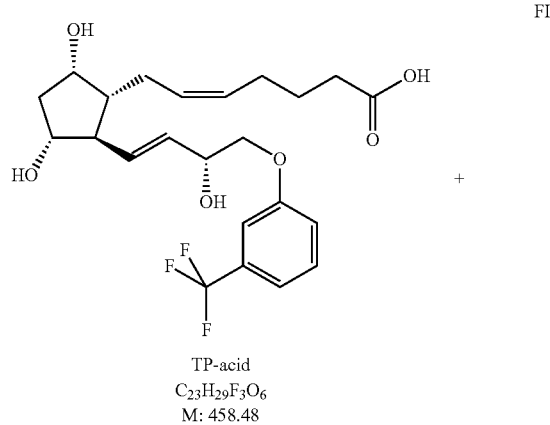

TP-acid
C₂₃H₂₉F₃O₆
M: 458.48

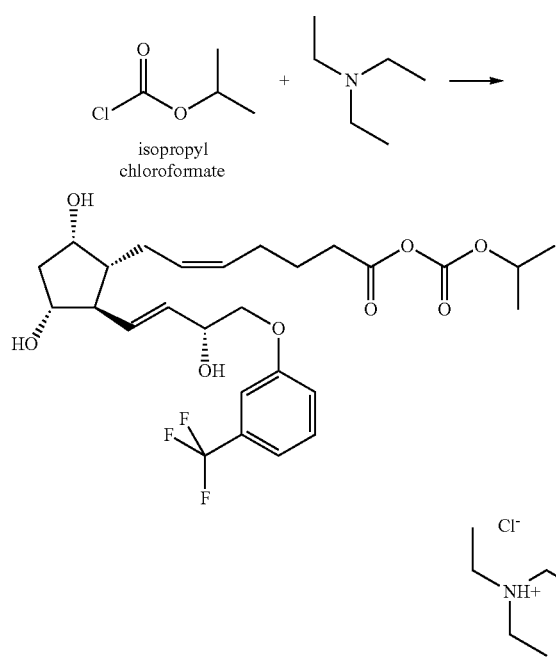

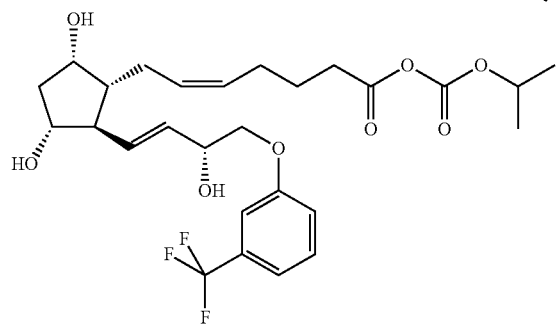

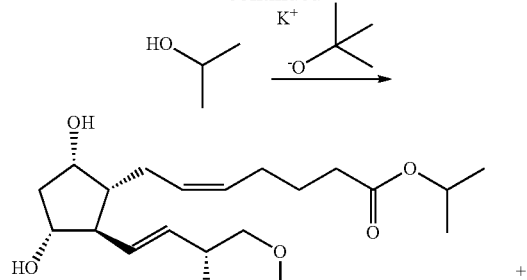

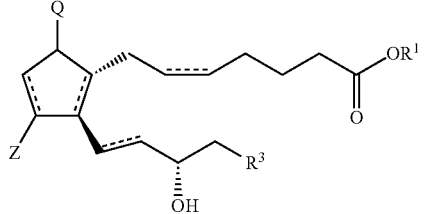

Travoprost
C₂₆H₃₅F₃O₆
M: 500.56

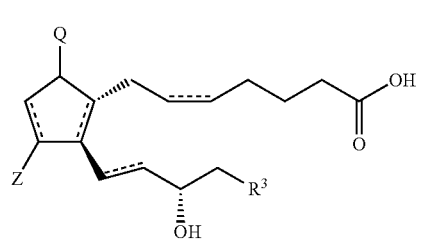

A further subject of our invention is process for the preparation of prostaglandin esters of the general formula (III).

(III)

where the meanings of the substituents are the followings:
the bonds in dotted lines may be single or double bonds, in the case of double bonds in positions 5,6 and 13,14 respectively, they may be in cis or in trans orientation,
Q and Z stand for hydroxyl group,
$R^1$ stands for straight or branched $C_{1-10}$ alkyl group,
$R^3$ stands for straight or branched, saturated or unsaturated $C_{4-6}$ hydrocarbon group, or a $C_{4-10}$ alkylcycloalkyl- or cycloalkyl group, or a phenyl-, $C_{7-10}$ alkylaryl-, or hetaryl- group optionally substituted with alkyl group, halogen atom or trifluoromethyl group,
Y means $(CH_2)_n$ group, or O or S atom, and
n=0-3.

The prostaglandin esters of the general formula (III) may be prepared in a way that an acid of the general formula (IV), (IV)

where in the formula the meanings of the dotted lines, Q, Z, $R^3$, Y and n are as defined above, a.) is activated with 2-chloro-1,3-dimethylimidazolinium chloride (DMC) and the resulting activated carboxylic acid intermediate is reacted with the alcohol of the general formula $R^1OH$, where the meaning of $R^1$ is as defined above, or b.) is reacted with straight or branched $C_{1-6}$ alkyl haloformate and the resulting mixed anhydride is reacted with the alcohol of the general formula R'OH, where the meaning of $R^1$ is as defined above, or c.) is activated with a straight or branched $C_{1-8}$ dialkyl dicarbonate and then in the presence of water-free magnesium salt reacted with the alcohol of the general formula $R^1OH$, where the meaning of $R^1$ is as defined above.

The travoprost acid of the formula (II) and prostaglandin acids of the general formula (IV)—for example latanoprost acid-contain free secondary hydroxyl groups in positions 9,11 and 15 which are esterificable and their protection seems to be necessary before esterification reaction.

Surprisingly it has been found that during the process according to our invention the intramolecular and intermolecular side reactions occur in low level without the protection of abovementioned free secondary hydroxyl groups and the isopropyl ester (formula (I)) and other esters of general formula (III)) are received with high yield.

According to our invention the alcohol component may also be activated to accelerate the reaction. Activation of the alcohol component may be carried out with metal alcoholates, as for metal alcoholate for example potassium tertiary-butoxide may be used.

In methods a.) and b.) according to our invention polar aprotic, aromatic, halogenated, ester- or ether-type solvents or the appropriate alcohol, preferably isopropyl alcohol, in method c.) acetonitrile may be used as solvent.

As alkyl haloformate straight or branched $C_{1-6}$ alkyl haloformates may be used. Use of isopropyl chloroformate is preferable but other chloro—or bromoformates are applicable The active carboxylic acid derivative is favourably formed at a temperature between 0-80° C., preferably at 0° C., and then reacted with the activated aliphatic primary or secondary alcohol at a temperature between 0-80° C., preferably at 70° C.

The active mixed anhydride is formed at a temperature between (−)10-40° C., preferably at room temperature, and then reacted with the aliphatic primary or secondary alcohol at a temperature between 0-80° C., preferably at 70° C.

In method c.) the active carboxylic acid derivative is formed at a temperature between 0-80° C., preferably at 25° C.

In method c.) as water-free magnesium salt, magnesium halogenides may be used. A typical representative is magnesium chloride.

The advantage of the process according to the invention is that for the isopropyl ester formation, instead of the toxic alkyl halogenide reagents known from the literature, the process according to our invention uses the alcohol itself as reagent and the applied activating agents are not toxic, either. In case of formation other esters of the general formula (III) the applied activating agents are not toxic as well.

Further details of the invention are demonstrated in the examples, without limiting the claims to the examples.

EXAMPLES

Example 1

300 mg (0.654 mmol) of travoprost-acid (compound of formula (II)) is dissolved in 6 ml of isopropanol. The solution is cooled to 0° C. Under stirring at that temperature, to the solution are added 59 mg potassium tertiary-butylate, 133 mg (0.785 mmol) of 2-chloro-1,3-dimethyl-imidazolinium chloride (DMC) activating agent and 274 µl (1.963 mmol) of triethylamine. The reaction mixture is gradually, in a period of 1 hour, heated to 70° C. and stirred at that temperature until the starting material disappears (approx. 1 hour). The reaction is followed by TLC.

Work-Up:

The reaction mixture is poured onto the mixture of isopropyl acetate and 1M $NaHSO_4$ solution. The phases are separated, the aqueous phase is washed twice with isopropyl acetate. The united organic phase is washed with 1 M $NaHCO_3$ solution, then with water, dried over $Na_2SO_4$, filtered and evaporated in vacuum. 289 mg (0,577 mmol) of travoprost (the compound of formula (I)) raw product is obtained, yield 88%.

The travoprost raw product is purified by chromatography on silica gel, using toluene-acetone eluent.

Example 2

300 mg (0.654 mmol) of travoprost-acid (compound of formula (II)) is dissolved in 6 ml of isopropanol. Under stirring at room temperature, to the solution are added 182 µl (1.309 mmol) of triethylamine and 982 µl (0,982 mmol) of 1 M solution of isopropyl chloroformate in toluene. The reaction mixture is stirred at 20-25° C. for 30 minutes, then cooled to −10±10° C. and the solution of 37 mg (0.327 mmol) of potassium tertiary-butylate in 2 ml of isopropanol is added to it. The reaction mixture is stirred at that temperature for 1 hour, then gradually, in a period of 1 hour, heated to 70° C. and stirred at that temperature until the starting material disappears (approx. 1 hour). The reaction is followed by TLC.

Work-Up:

The reaction mixture is poured onto the mixture of isopropyl acetate and 1M $NaHSO_4$ solution. The phases are separated, the aqueous phase is washed twice with isopropyl acetate. The united organic phase is washed with 1 M $NaHCO_3$ solution, then with water, dried over $Na_2SO_4$, filtered and evaporated in vacuum. 285 mg (0,569 mmol) of travoprost (the compound of formula (I)) raw product is obtained, yield 87%. The raw product is purified by chromatography on silica gel, using hexane-isopropyl acetate eluent.

Example 3

6.3 mg (0.066 mmol) of water-free magnesium chloride, 143 mg (0.654 mmol) of di-tert-butyl dicarbonate and 300 mg (0.654 mmol) of travoprost-acid (compound of formula (II)) are stirred in 1 ml of acetonitrile, then 100 ml (1.31 mmol) of isopropanol is added and the mixture is stirred overnight. The reaction is followed by TLC.

Work-Up:

The reaction mixture is poured onto the mixture of isopropyl acetate and 1M $NaHSO_4$ solution. The phases are separated, the aqueous phase is washed twice with isopropyl acetate. The combined organic phase is washed with 1 M $NaHCO_3$ solution, then with water, dried over $Na_2SO_4$, filtered and evaporated in vacuum. 270 mg (0,539 mmol) of travoprost raw product is obtained, yield 82%. The travoprost (compound of formula (I)) raw product is purified by chromatography on silica gel, using toluene-acetone eluent.

Example 4

255.2 mg (0.654 mmol) of latanoprost acid (compound of formula (IV where Q and Z are hydroxyl groups and R3 is a benzyl functional group and in 13,14 position there is no double bond)) is dissolved in 6 ml of isopropanol. The solution is cooled to 0° C. Under stirring at that temperature, to the solution are added 59 mg potassium tertiary-butylate, 133 mg (0.785 mmol) of 2-chloro-1,3-dimethyl-imidazolinium chloride (DMC) activating agent and 274 d (1.963 mmol) of triethylamine. The reaction mixture is gradually, in a period of 1 hour, heated to 70° C. and stirred at that temperature until the starting material disappears (approx. 1 hour). The reaction is followed by TLC.

Work-Up:

The reaction mixture is poured onto the mixture of isopropyl acetate and 1M $NaHSO_4$ solution. The phases are separated, the aqueous phase is washed twice with isopropyl acetate. The united organic phase is washed with 1 M $NaHCO_3$ solution, then with water, dried over $Na_2SO_4$, filtered and evaporated in vacuum. 230 mg (0,532 mmol) of latanoprost raw product is obtained, yield 81.3%.

The latanoprost raw product is purified by chromatography on silica gel, using diisopropyl ether-acetone eluent.

The invention claimed is:

1. Process for the preparation travoprost of formula (I)

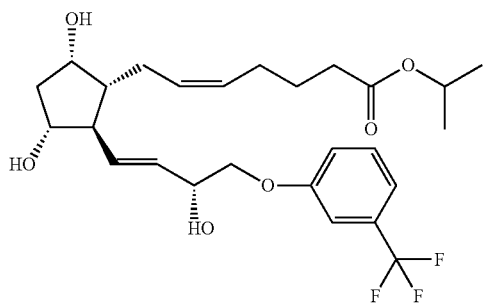

(I)

wherein the free acid of formula (II)

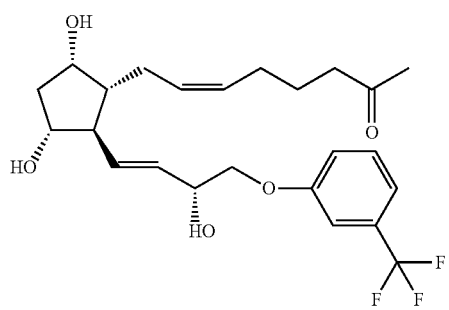

(II)

is
a.) activated with 2-chloro-1,3-dimethylimidazolinium chloride (DMC) and the resulting activated carboxylic acid intermediate is reacted with optionally activated isopropyl alcohol, or
b.) activated with a straight or branched $C_{1-6}$ alkyl haloformate and the resulting mixed anhydride is reacted with optionally activated isopropyl alcohol, or
c.) activated with a straight or branched $C_{1-8}$ dialkyl dicarbonate and reacted with optionally activated isopropyl alcohol in the presence of water-free magnesium salt.

2. Process for the preparation of prostaglandin esters of the general formula (III),

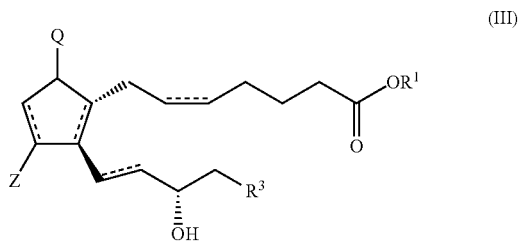

(III)

wherein:
the bonds in dotted lines may be single or double bonds, in the case of double bonds in positions 5,6 and 13,14 respectively, they may be in cis or in trans orientation,
Q and Z stand for hydroxyl group,
$R^1$ stands for straight or branched $C_{1-10}$ alkyl group,
$R^3$ stands for straight or branched, saturated or unsaturated $C_{4-6}$ hydrocarbon group, or a $C_{4-10}$ alkylcycloalkyl or cycloalkyl group, or a phenyl, $C_{7-10}$ alkylaryl, or hetaryl group optionally substituted with alkyl group, halogen atom or trifluoromethyl group,
wherein an acid of the general formula (IV),

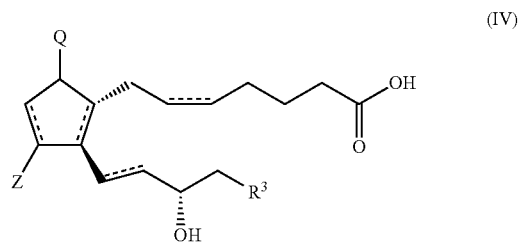

(IV)

in which Q, Z, and $R^3$ are as defined above,
a.) is activated with 2-chloro-1,3-dimethylimidazolinium chloride (DMC) and the resulting activated carboxylic acid intermediate is reacted in the presence of base with an optionally activated alcohol of the general formula $R^1OH$, where the meaning of $R^1$ is as defined above, or
b.) is activated with a straight or branched $C_{1-6}$ alkyl haloformate and the resulting mixed anhydride is reacted with an optionally alcohol of the general formula $R^1OH$, where the meaning of $R^1$ is as defined above, or
c.) is activated with a straight or branched $C_{1-8}$ dialkyl dicarbonate and then in the presence of water-free magnesium salt reacted with an optionally activated alcohol of the general formula $R^1OH$, where the meaning of $R^1$ is as defined above.

3. The process as defined in claim 1, wherein the preparation of the activated carboxylic acid intermediate is carried out in the presence of polar aprotic, aromatic, halogenated, ester- or ether-type, or the appropriate alcohol solvent.

4. The process as defined in claim 1, wherein the preparation of the activated mixed anhydride intermediate is carried out in the presence of polar aprotic, aromatic, halogenated, ester- or ether-type, or the appropriate alcohol solvent.

5. The process as defined in claim 1, wherein the preparation of the activated carboxylic acid intermediate is carried out in the presence of polar aprotic, aromatic, halogenated, ester- or ether-type solvent.

6. The process as defined in claim 3, wherein isopropyl alcohol is applied as solvent.

7. The process as defined in claim 5, wherein acetonitrile is applied as solvent.

8. The process as defined in claim 1, wherein the activated carboxylic acid derivative is formed at a temperature between 0-80° C.

9. The process as defined in claim 1, wherein the activated mixed anhydride is formed at a temperature between (−)10-40° C.

10. The process as defined in claim 1, wherein the activated carboxylic acid derivative is formed at a temperature between 0-80° C.

11. The process as defined in claim 2, wherein an activated alcohol is applied as the alcohol.

12. The process as defined in claim 11, wherein the alcohol component is activated with a metal alcoholate.

13. The process as defined in claim 12, wherein an alcoholate potassium tertiary-butoxide is applied as a metal alcoholate.

14. The process as defined in claim 1, wherein magnesium chloride is applied as the water-free magnesium salt.

15. The processes according to method c.) of claim 1, wherein activation is carried out using di-tertiary-butyl dicarbonate.

16. The process as defined in claim 1, wherein the activated carboxylic acid derivative is formed at a temperature at 0° C.

17. The process as defined in claim 1, wherein the activated mixed anhydride is formed at room temperature.

18. The process as defined in claim 1, wherein the activated carboxylic acid derivative is formed at a temperature of 25° C.

19. The process as defined in claim 2, characterized by that the preparation of the activated carboxylic acid intermediate is carried out in the presence of polar aprotic, aromatic, halogenated, ester- or ether-type, or the appropriate alcohol solvent.

20. The process as defined in claim 2, characterized by that the preparation of the activated mixed anhydride intermediate is carried out in the presence of polar aprotic, aromatic, halogenated, ester- or ether-type, or the appropriate alcohol solvent.

21. The process as defined in claim 1, wherein said optionally activated isopropyl alcohol is activated isopropyl alcohol.

* * * * *